(12) United States Patent
Wu et al.

(10) Patent No.: US 9,933,390 B2
(45) Date of Patent: Apr. 3, 2018

(54) DEVICES FOR EXTRACTING AT LEAST ONE ANALYTE

(71) Applicant: Agency for Science, Technology and Research, Singapore (SG)

(72) Inventors: Ruige Wu, Singapore (SG); Pin Chuan Chen, Singapore (SG); Zhiping Wang, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 344 days.

(21) Appl. No.: 14/647,346

(22) PCT Filed: Dec. 13, 2013

(86) PCT No.: PCT/SG2013/000532
§ 371 (c)(1),
(2) Date: May 26, 2015

(87) PCT Pub. No.: WO2014/092652
PCT Pub. Date: Jun. 19, 2014

(65) Prior Publication Data
US 2015/0323498 A1     Nov. 12, 2015

(30) Foreign Application Priority Data

Dec. 14, 2012   (SG) ................................ 201209243-3

(51) Int. Cl.
*G01N 27/447*     (2006.01)
*C12Q 1/68*     (2018.01)

(52) U.S. Cl.
CPC ..... *G01N 27/44739* (2013.01); *C12Q 1/6806* (2013.01); *G01N 27/44778* (2013.01);
(Continued)

(58) Field of Classification Search
CPC ....... G01N 27/44739; G01N 27/44778; G01N 27/44791; G01N 27/44726; G01N 27/44721; C12Q 1/6806
See application file for complete search history.

(56) References Cited

U.S. PATENT DOCUMENTS 8,046,043 B2    10/2011    Asano et al.
2005/0034990 A1    2/2005    Crooks et al.
(Continued)

FOREIGN PATENT DOCUMENTS

EP     1542788 B1     9/2006

OTHER PUBLICATIONS

International Preliminary Report on Patentability for International Application No. PCT/SG2013/000532 dated Nov. 7, 2014, pp. 1-3.

*Primary Examiner* — J. Christopher Ball
(74) *Attorney, Agent, or Firm* — Winstead, P.C.

(57) ABSTRACT

A device for extracting at least one analyte may include: a sample reservoir configured to contain a sample comprising at least one target analyte and interfering materials; at least one extraction chamber connected to the sample reservoir; at least one porous structure lining one or more sides of the at least one extraction chamber; and a voltage source configured to provide a first voltage and a second voltage, wherein, when the first voltage is provided, the at least one target analyte and the interfering materials move towards the at least one extraction chamber or to a predetermined area from the at least one extraction chamber, wherein, when the second voltage is provided, the interfering materials pass through and exit the at least one extraction chamber, and the at least one target analyte is stopped from exiting the at least one extraction chamber by means of the at least one porous structure.

18 Claims, 13 Drawing Sheets

(52) U.S. Cl.
 CPC .  *G01N 27/44791* (2013.01); *G01N 27/44721* (2013.01); *G01N 27/44726* (2013.01)

(56) References Cited

U.S. PATENT DOCUMENTS

| | | |
|---|---|---|
| 2007/0231790 A1 | 10/2007 | Su |
| 2013/0224846 A1 | 8/2013 | Jovanovich et al. |
| 2013/0236907 A1 | 9/2013 | Petersen et al. |

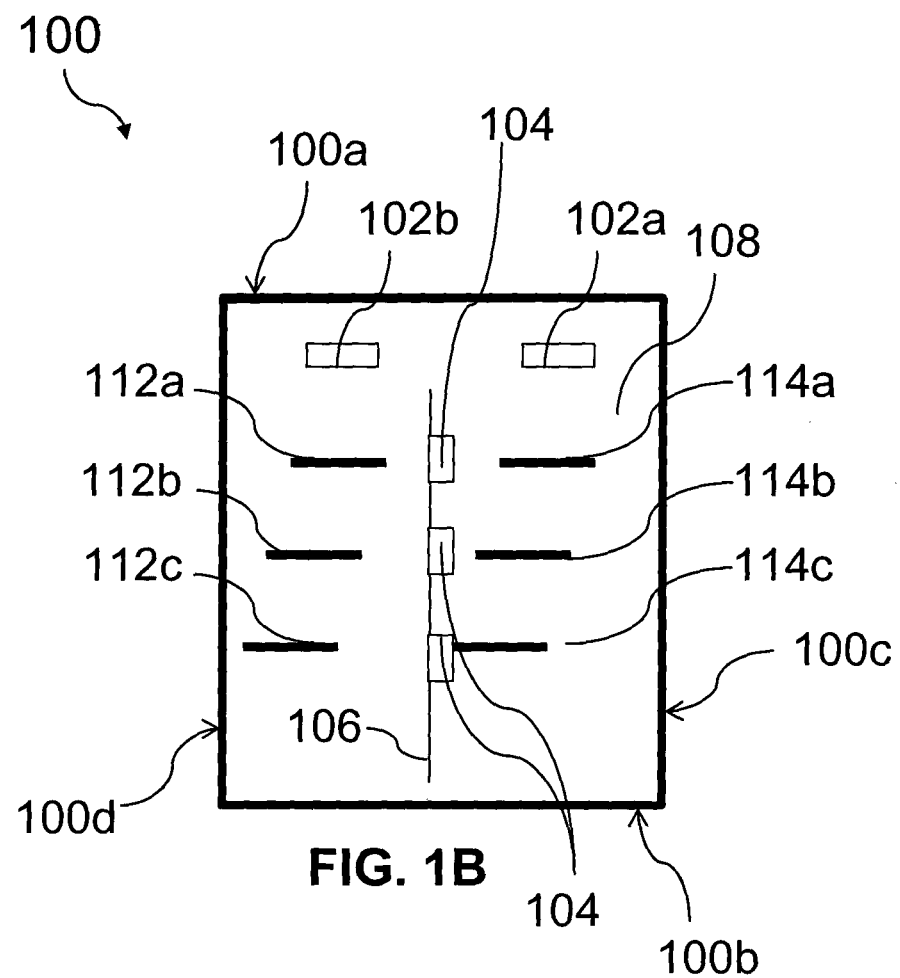
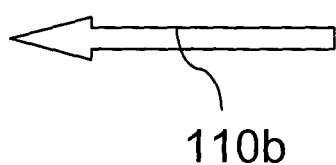
FIG. 1B

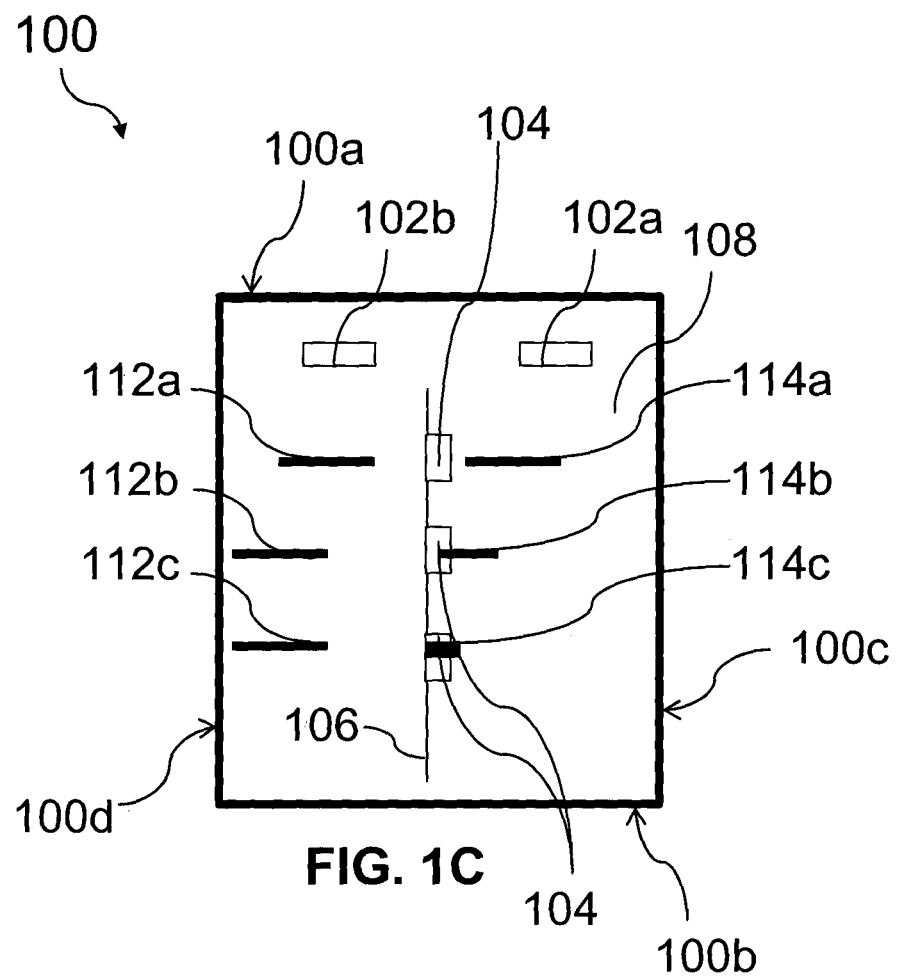
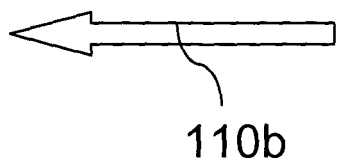
FIG. 1C

500

600

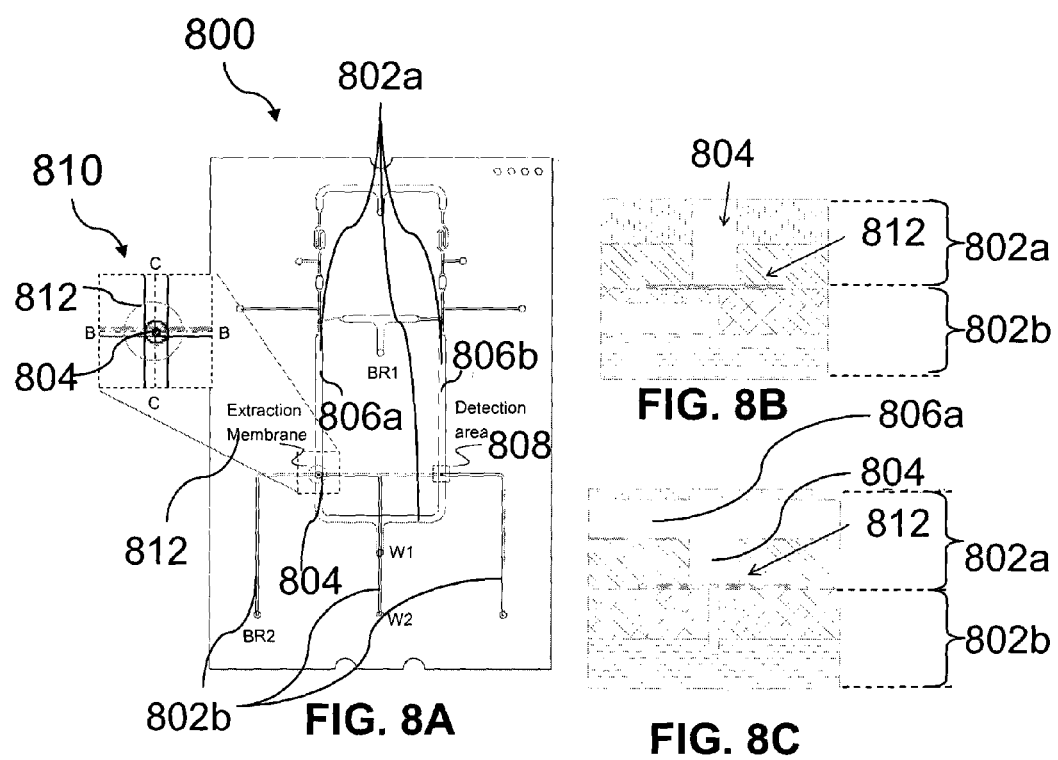

DEVICES FOR EXTRACTING AT LEAST ONE ANALYTE

TECHNICAL FIELD

Various aspects relate to devices for extracting at least one analyte.

BACKGROUND

A pure analyte (DNA, RNA or protein) fragment is important for bioanalysis. Preparation of a pure analyte fragment from a complicated sample may include separation of the target analyte fragment from interfering materials by gel electrophoresis and extraction of it from the gel matrix. To get pure target analyte fragment, the gel with all separated fragments is placed on an ultraviolet (UV) light box to visualize the location of the interested analyte fragments. A scalpel is used to cut around the interested fragment band and carefully slice the small piece of gel containing the interested band from the whole gel. After that, the sliced gel is put in a centrifuge tube with other chemicals to obtain the pure analyte fragment.

Since UV light is dangerous to the eyes and skin, protection (e.g. a protective shield and/or protective clothing) may be needed for an operator performing the separation and extraction of the target analyte fragment. Furthermore, the above-described approach to preparing and extracting the target analyte fragment (e.g. to obtain a pure analyte fragment) may be time consuming and laborious. Even further, the above-described approach cannot be done automatically and the results are operator dependent. New ways of extracting a target analyte fragment may be needed.

SUMMARY

In an embodiment, a device for extracting at least one analyte may include: a sample reservoir configured to contain a sample comprising at least one target analyte and interfering materials; at least one extraction chamber connected to the sample reservoir; at least one porous structure lining one or more sides of the at least one extraction chamber; and a voltage source configured to provide a first voltage and a second voltage, wherein, when the first voltage is provided, the at least one target analyte and the interfering materials move towards the at least one extraction chamber or to a predetermined area from the at least one extraction chamber, wherein, when the second voltage is provided, the interfering materials pass through and exit the at least one extraction chamber, and the at least one target analyte is stopped from exiting the at least one extraction chamber by means of the at least one porous structure.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various, aspects of the invention are described with reference to the following drawings, in which:

FIG. 1A to FIG. 1C show plan-views of a device for extracting at least one analyte.

FIG. 8A to FIG. 8C show various views of a multi-layer microfluidic chip including at least one porous structure.

DESCRIPTION

Figure 1A:
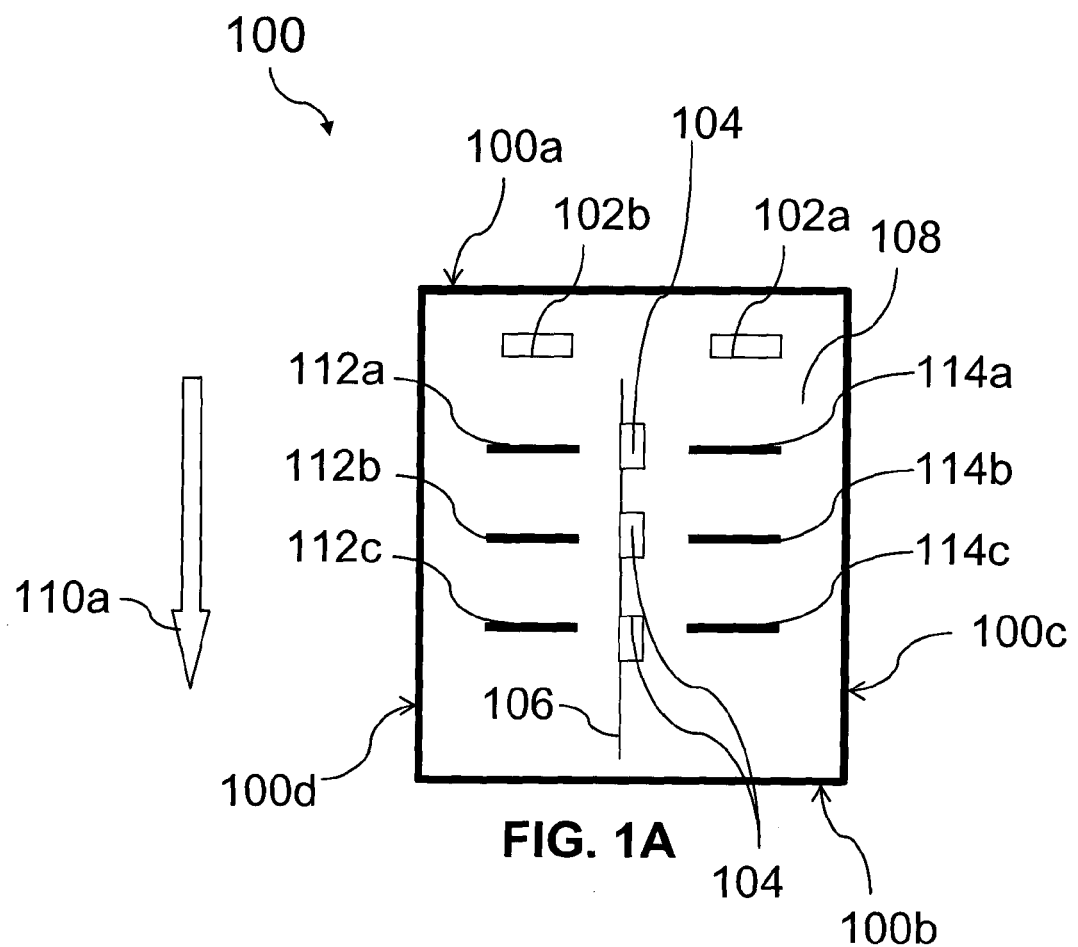

The following detailed description refers to the accompanying drawings that show, by way of illustration, specific details and aspects in which the invention may be practised. These aspects are described in sufficient detail to enable those skilled in the art to practice the invention. Other aspects may be utilized and structural, logical, and electrical changes may be made without departing from the scope of the invention. The various aspects are not necessarily mutually exclusive, as some aspects can be combined with one or more other aspects to form new aspects. Various aspects are described for structures or devices, and various aspects are described for methods. It may be understood that one or more (e.g. all) aspects described in connection with structures or devices may be equally applicable to the methods, and vice versa.

The word "exemplary" is used herein to mean "serving as an example, instance, or illustration". Any aspect or design described herein as "exemplary" is not necessarily to be construed as preferred or advantageous over other aspects or designs.

The terms "coupled" and/or "connected" used herein to describe a feature being connected to at least one other implied feature, are not meant to mean that the feature and the at least one other implied feature must be directly coupled or connected together; intervening features may be provided between the feature and at least one other implied feature.

Directional terminology, such as e.g. "upper", "lower", "top", "bottom", "left-hand", "right-hand", etc., may be used with reference to the orientation of figure(s) being described. Because components of the figure(s) may be positioned in a number of different orientations, the directional terminology is used for purposes of illustration and is in no way limiting. It is to be understood that structural or logical changes may be made without departing from the scope of the invention.

Bioanalysis may include analysis of an analyte and/or an analyte fragment (e.g. DNA, RNA and/or protein). The description that follows provides examples of preparation, separation, and extraction of an analyte fragment (e.g. pure analyte fragment). However, the examples described may be analogously applied to preparation, separation, and extraction of an analyte (e.g. pure analyte).

Preparation of a pure analyte fragment from a sample (e.g. a sample including, or consisting of, the pure analyte fragment as well as other interfering materials) may include separating the pure analyte fragment from the interfering materials, e.g. by means of a separation process. The pure analyte fragment may also be referred to as a target analyte fragment.

The separation process may include, or may be, electrophoresis (e.g. gel electrophoresis). The separation process (e.g. electrophoresis, e.g. gel electrophoresis) may be performed in a medium. For example, in gel electrophoresis, the medium in which the separation process is performed may include, or may be, a gel matrix.

Preparation of the pure analyte fragment from the sample (e.g. a complicated sample including, or consisting of, the pure analyte fragment as well as other interfering materials) may further include extracting the target analyte fragment from the medium in which the separation process is performed (e.g. gel matrix). The extraction may be performed subsequent to the separation process (e.g. electrophoresis, e.g. gel electrophoresis).

In order to obtain a pure target analyte fragment, the medium (e.g. gel matrix) including the target analyte fragment as well as other separated analyte fragments may be placed on a surface that may be illuminated by ultraviolet (UV) light (e.g. a UV light box). This may be done in order to visualize the location of the target analyte fragment in the medium (e.g. gel matrix).

An implement (e.g. a scalpel) may be used to cut around the location of the target analyte fragment. The area around the location of the target analyte fragment may be, or may be referred to as, a band. The band having the target analyte fragment may be sliced from the medium (e.g. gel matrix) and the target analyte fragment may thereafter be extracted from the sliced band. For example, the sliced band having the target analyte fragment may be placed in a centrifuge (e.g. a centrifuge tube), e.g. with other chemicals, to obtain a pure analyte fragment.

As described above, UV light may be used to visualize the location of the target analyte fragment in the medium (e.g. gel matrix). Since UV light is dangerous to the eyes and skin, protection (e.g. a protective shield and/or protective clothing) may be needed for an operator performing the separation and extraction of the target analyte fragment. Furthermore, the above-described approach to preparing and extracting the target analyte fragment (e.g. to obtain a pure analyte fragment) may be time consuming and laborious. Even further, the above-described approach cannot be done automatically and the results are operator dependent.

Accordingly, it may be desirable to provide a method and/or device that may be simpler and safer than the current state-of-the art technology for analyte fragment extraction from a medium (e.g. gel matrix).

It may be desirable to provide a method and/or device that may select and/or extract a target analyte fragment automatically out of a medium (e.g. gel matrix) without use of UV light.

It may be desirable to provide a method and/or device that may enable an operator to only load a sample (e.g. complicated sample having the target analyte fragment and interfering materials) into a medium (e.g. gel matrix) and automatically collect the target analyte fragment (e.g. desired analyte fragment). In other words, it may be desirable to provide a method and/or device that may not be operator dependent.

FIG. 1A to FIG. 1C show plan-views of a device 100 for extracting at least one analyte.

The device 100 may be simpler and safer than the current state-of-the art technology for analyte fragment extraction from a medium (e.g. gel matrix).

The device 100 may be used to select and/or extract a target analyte fragment (e.g. a desired analyte fragment) automatically out of a medium (e.g. gel matrix) without use of UV light.

The device 100 may enable an operator to only load a sample (e.g. complicated sample having the target analyte fragment and interfering materials) into a medium (e.g. gel matrix) and automatically collect the target analyte fragment (e.g. desired analyte fragment).

The device 100 may be included in a detection system, that may detect the movement of analyte fragments in electrophoresis (e.g. gel electrophoresis) and trigger an extraction of a target analyte fragment when the target analyte fragment is detected (e.g. movement of the target analyte fragment is detected).

The device 100 may include a sample reservoir 102a, at least one extraction chamber 104, and at least one porous structure 106 lining one or more sides of the at least one extraction chamber 104. The device 100 may further include a reference reservoir 102b.

In the embodiment shown in FIG. 1A, only three extraction chambers 104 are shown as an example. However, in another embodiment, the number of extraction chambers may be less than three (e.g. one, two) or more than three (e.g. four, five, six, etc.).

In the embodiment shown in FIG. 1A, one porous structure 106 is shown to line one side of the at least one extraction chamber 104. However, in another embodiment, the at least one porous structure 106 may line more than one side of the at least one extraction chamber 104.

A sample (e.g. having a target analyte fragment and interfering materials) and a reference (e.g. having a reference analyte fragment, e.g. having molecules of the same size as the target analyte fragment of the sample) may be loaded into respective reservoirs. For example, a reference containing a reference analyte fragment (e.g. having molecules of the same size as the target analyte fragment of the sample) may be loaded in the reference reservoir 102b, and a sample (e.g. having a target analyte fragment and interfering materials) may be loaded in the sample reservoir 102a.

Accordingly, the sample reservoir 102a may be configured to contain a sample including at least one target analyte or target analyte fragment and interfering materials, and the reference reservoir 102b may be configured to contain a reference analyte or reference analyte fragment, which may have particles of the same size as the target analyte fragment of the sample.

Electrodes (not shown in FIG. 1A) may be placed in a buffer solution to form an electrical field that may drive the target analyte fragment and the reference analyte fragment to move in a medium 108 (e.g. a gel or gel matrix) based on the electrophoresis principle. For example, the target analyte fragment and the reference analyte fragment may move under the influence of the electrical field from the sample and reference reservoirs towards a predetermined area near the at least one extraction chamber 104. The at least one extraction chamber 104 may be connected to the sample reservoir 102a and the reference reservoir 102b by means of the medium 108 (e.g. gel matrix). Accordingly, the target analyte fragment and the reference analyte fragment may move through the medium 108 (e.g. gel matrix) towards a predetermined area near the at least one extraction chamber 104.

For example, as shown in FIG. 1A, an electrical field may be formed in the direction indicated by arrow 110a (e.g. by means of placing electrodes at sides 100a, 100b of the device 100). After running electrophoresis (e.g. gel electrophoresis) for a period of time, analyte fragments with different size may be separated as shown in FIG. 1A. The reference analyte fragments separated by means of electrophoresis (e.g. gel electrophoresis) are indicated in FIG. 1A and FIG. 1B as reference signs 112a, 112b, 112c; and the separated target analyte fragments of the sample are indicated in FIG. 1A and FIG. 1B as reference signs 114a, 114b, 114c.

Accordingly, the target analyte fragment and the interfering materials of the sample may move under the influence of the voltage applied to the device 100 to a predetermined area from or near the at least one extraction chamber 104.

A detector may detect the separation of the reference analyte fragments 112a, 112b, 112c. For example, a detector may detect the reference analyte fragments 112a, 112b, 112c when the reference analyte fragments 112a, 112b, 112c are at least substantially aligned to the at least one extraction chamber 104. Substantial alignment of the reference analyte fragments 112a, 112b, 112c to the at least one extraction chamber 104 may imply that the separated target analyte fragments (indicated by reference signs 114a, 114b, 114c) of the sample are also at least substantially aligned to the at least one extraction chamber 104, as shown in FIG. 1B.

Upon detection of the separated reference analyte fragments 112a, 112b, 112c, a trigger may switch the direction of the electrical field. For example, as shown in FIG. 1B, the electrical field may be switched to the direction indicated by arrow 110b (e.g. by means of placing electrodes at sides 100c, 100d of the device 100) from the direction indicated by arrow 110a shown in FIG. 1A. At this time, the target analyte fragments and the interfering materials (indicated by reference signs 114a, 114b, 114c) may move towards the at least one extraction chamber 104 under the influence of the electrical field 110b. Since the direction of the electrical field may be switched when the separated target analyte fragments (indicated by reference signs 114a, 114b, 114c) of the sample are also at least substantially aligned to the at least one extraction chamber 104, the at least one extraction chamber 104 may be located along the flow path of the target analyte fragments and the interfering materials (indicated by reference signs 114a, 114b, 114c) when the electrical field is oriented in the direction indicated by arrow 110b.

The at least one porous structure 106 lining one or more sides of the at least one extraction chamber 104 may have a suitable pore size which can permit small molecules like dyes and ions to pass through under electrical field, while big analyte fragments will be stopped from passing through it. Accordingly, the at least one porous structure 106 lining one or more sides of the at least one extraction chamber 104 may stop the target analyte fragment from passing through it and thus may act as a means to contain the target analyte fragment in the at least one extraction chamber 104. The at least one porous structure 106 lining one or more sides of the at least one extraction chamber 104 may include, or may be, an extraction membrane (e.g. a porous extraction membrane).

Accordingly, the interfering materials may pass through the at least one porous structure 106 lining one- or more sides of the at least one extraction chamber 104, and may exit the at least one extraction chamber 104 under the influence of the voltage applied to the device 100 in the direction indicated by arrow 110b. As shown in FIG. 1C, the target analyte fragment may be stopped or prevented from exiting the at least one extraction chamber 104 by means of the at least one porous structure 106 lining one or more sides of the at least one extraction chamber 104. Once all the target analyte fragments are extracted from the medium 108 (e.g. gel or gel matrix), a pipette can be used to collect the desired analyte fragments from the at least one extraction chamber 104.

Figure 2:
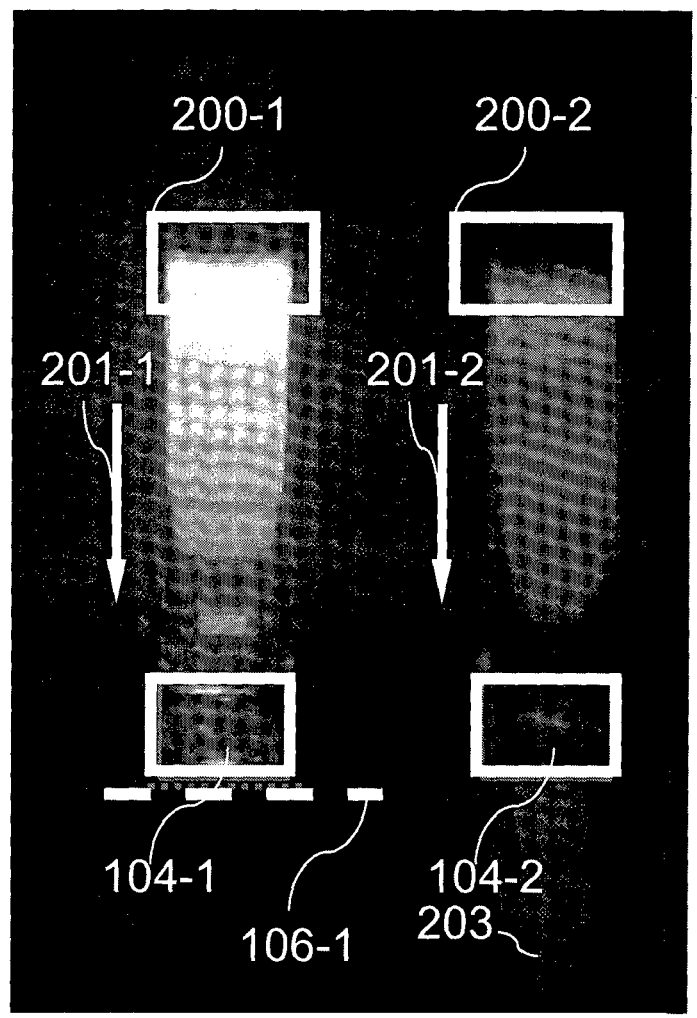
FIG. 2 shows a result of using the device shown in FIG. 1A to FIG. 1C for an extraction experiment.

FIG. 2 shows a result of using the device 100 shown in FIG. 1A to FIG. 1C for an extraction experiment.

A molecular-weight size marker including a DNA ladder of at least 100 bp was used for the extraction experiment. FIG. 2 shows a first reservoir 200-1 and a second reservoir 200-2. The first reservoir 200-1 is at least substantially aligned to a first extraction chamber 104-1 and a porous structure 106-1 lining one side of the first extraction chamber 104-1. A target analyte fragment contained in the first reservoir 200-1 flows along a first flow path 201-1 from the first reservoir 200-1 to the first extraction chamber 104-1, e.g. under the influence of an applied voltage.

FIG. 2 also shows that the second reservoir 200-2 is at least substantially aligned to a second extraction chamber 104-2. The second extraction chamber 104-2 is free from a porous structure. A target analyte fragment contained in the second reservoir 200-2 flows along a second flow path 201-2 from the second reservoir 200-2 to the second extraction chamber 104-2, e.g. under the influence of an applied voltage.

As shown in FIG. 2, in the first flow path 201-1 having the porous structure 106-1 (e.g. extraction membrane), all DNA fragments no smaller than about 100 bp were stopped in the extraction chamber 104-1, e.g. by means of the porous structure 106-1. This is indicated by the containment of the sample in the extraction chamber 104-1. However, in the second flow path 201-2 free from the porous structure, the DNA fragments passed through the extraction chamber 104-2 and moved towards the electrode (e.g. anode) under the electrical field. This is indicated in FIG. 2 as a bleeding 203 from the extraction chamber 104-2 away from the second reservoir 200-2.

In an embodiment, the device 100 may include, or may be, a cartridge 300.

FIG. 3A and FIG. 3B show perspective view of a cartridge 300 including a plurality of extraction chambers 302-1 to 302-3, a membrane frame 304, a chamber frame 306, and a sandwiched porous structure 308.

The cartridge 300 may be included in a detection system that may detect the movement of analyte fragments in electrophoresis (e.g. gel electrophoresis) and trigger an extraction of a target analyte fragment when the target analyte fragment is detected (e.g. movement of the target analyte fragment is detected). The sandwiched porous structure 308 may include or may be a sandwiched membrane.

The chamber frame 306 may be designed to assist the integration of the porous structure 308 (e.g. membrane) into the plurality of extraction chambers 302-1 to 302-3. For example, the chamber frame 306 may be designed to line at least one side of the plurality of extraction chambers 302-1 to 302-3 with the porous structure 308 (e.g. membrane).

At first, the cartridge 300 may be used for gel casting as a gel container. At first, the porous structure 308 (e.g.

membrane) may be sandwiched between the membrane frame 304 and the chamber frame 306, as shown in FIG. 3B. It may then be dipped into casted gel in cartridge 300. After the gel is solidified, the chamber frame 306 may be removed, leaving the membrane frame 304, the porous structure 308 (e.g. membrane) and the formed plurality of extraction chambers 302-1 to 302-3 inside the gel, as shown in FIG. 3A. A plurality of porous structures 308 (e.g. membranes) can be formed, with each extraction chamber of the plurality of extraction chambers 302-1 to 302-3 having a respective porous structure 308. Alternatively, or in addition, as shown in FIG. 3A and FIG. 3B, a single porous structure 308 (e.g. membrane) can be used for all extraction chambers of the plurality of extraction chambers 302-1 to 302-3.

As described above, the device 100 (e.g. cartridge 300) may be included in a detection system that may detect the movement of analyte fragments in electrophoresis (e.g. gel electrophoresis) and trigger an extraction of a target analyte fragment when the target analyte fragment is detected (e.g. movement of the target analyte fragment is detected).

Figure 4:
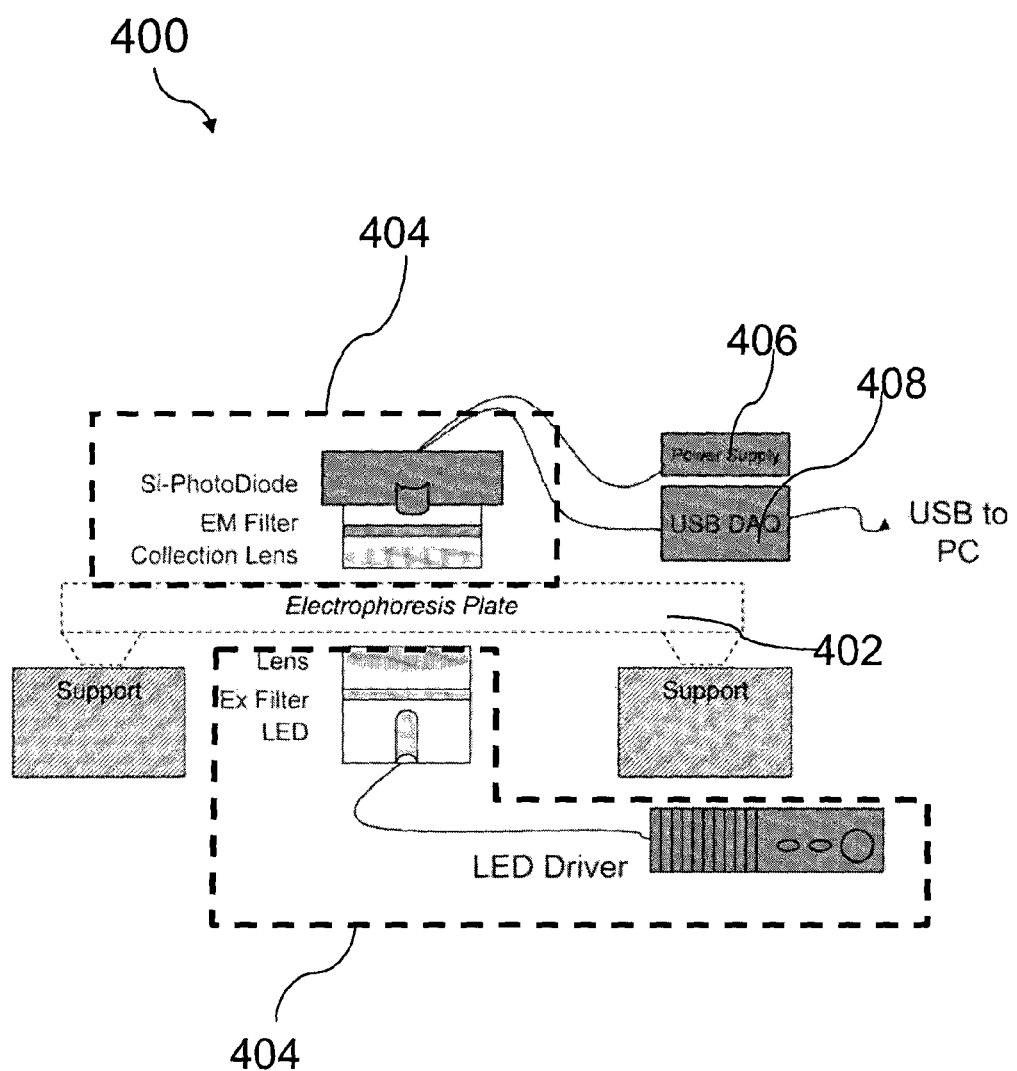
FIG. 4 shows a schematic of a detection system that may detect the movement of analyte fragments in electrophoresis and trigger an extraction of a target analyte fragment.

FIG. 4 shows a schematic of a detection system 400 that may detect the movement of analyte fragments in electrophoresis (e.g. gel electrophoresis) and trigger an extraction of a target analyte fragment when the target analyte fragment is detected (e.g. movement of the target analyte fragment is detected).

The detection system 400 may include a platform 402 where the extraction is performed, a detection system 404 to locate the reference analyte fragment to trigger the switch of electrical field direction, a power supply 406, a data collection module 408, and a voltage switch device (not shown in FIG. 4).

Figure 5:
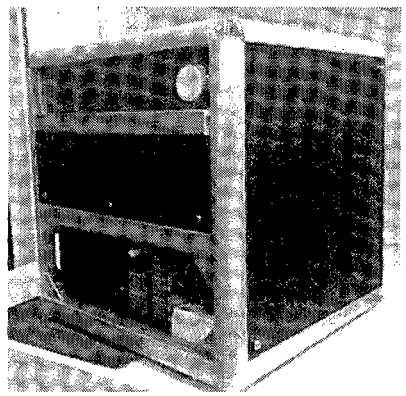
FIG. 5 shows an electrophoresis and detection system which may be used for separation and extraction of a target analyte fragment from a sample.

FIG. 5 shows an electrophoresis and detection system 500 which may be used for separation and extraction of a target analyte fragment from a sample. The electrophoresis and detection system 500 may be identified with the detection system 400 shown in FIG. 4. In other words, the detection system 400 shown in FIG. 4 may be a schematic of the detection system 500 shown in FIG. 5.

Figure 6:
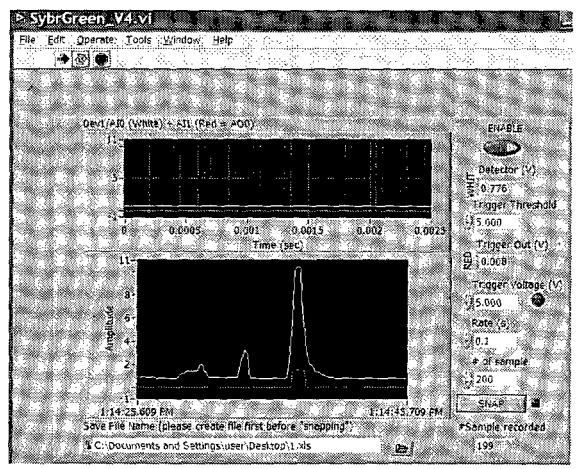
FIG. 6 shows a user interface of a software to detect the reference analyte fragment and trigger the switch of electrical field direction.

FIG. 6 shows a user interface of a software to detect the reference analyte fragment and trigger the switch of electrical field direction.

An experiment was carried out to demonstrate multiple DNA extraction using the device 100 (e.g. cartridge 300) and the detection system 400. The results of the experiment are shown in FIG. 7A to FIG. 7C.

Figure 3:
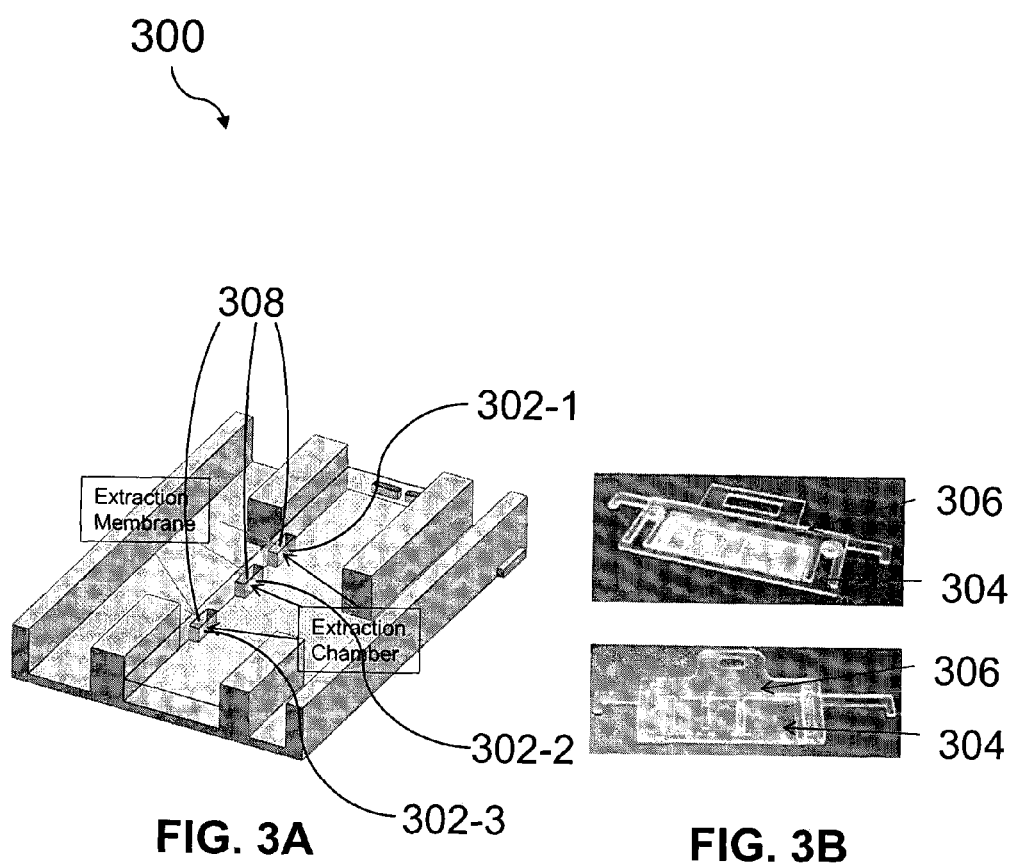
FIG. 3A and FIG. 3B show perspective view of a cartridge including a plurality of extraction chambers, a membrane frame, a chamber frame, and a sandwiched porous structure.
Figure 7A:
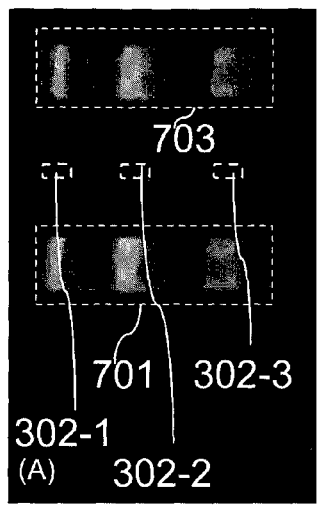
FIG. 7A to FIG. 7C show reference DNA fragments and target DNA fragments that may be separated by means of the cartridge shown in FIG. 3 and the detection system shown in FIG. 4 and FIG. 5.
Figure 7B:
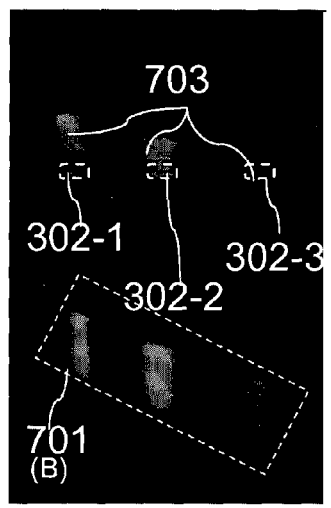
Figure 7C:
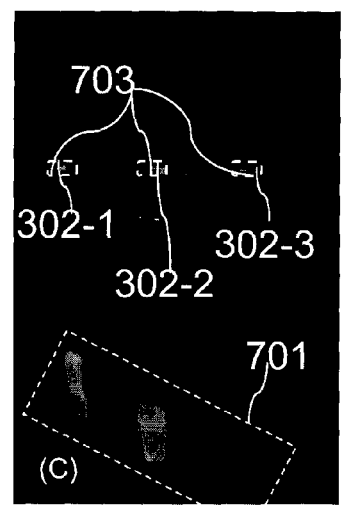

FIG. 7A to FIG. 7C show reference DNA fragments 701 and target DNA fragments 703 that may be separated by means of the cartridge 300 shown in FIG. 3 and the detection system shown in FIG. 4 and FIG. 5.

As shown in FIG. 7A to FIG. 7C, extraction of three DNA fragments (200 bp, 500 bp and 1 kb), was realized with the cartridge 300 shown in FIG. 3. After automatically switching the direction of electrical field with the trigger system, the three target DNA fragments 703 moved towards the respective extraction chamber 302-1, 302-2, 302-3. To visualize and verify the extraction process, both reference DNA fragments 701 and target DNA fragments 703 were mixed with fluorescent dye SYBR green I.

DNA quantitation of extracted DNA fragment was performed using Nanodrop 2000. The A260/A280 ratio of three extracted DNA fragment were all about 1.8, which shows that the purity of collected DNA fragment is acceptable and there may not be a need for an extra purification step. Therefore, the device 100 (e.g. cartridge 300) and the detection system 400 can help operators extract several separated target DNA fragments from a medium (e.g. gel or gel matrix) and avoid the use of hazardous UV light.

In an embodiment, extraction of one or more target analytes and/or target analyte fragments may be realized on a device configured as a multi-layer microfluidic chip.

FIG. 8A shows a plan view of a multi-layer microfluidic chip 800 including at least one porous structure 812.

FIG. 8B shows a cross-sectional view of the multi-layer microfluidic chip 800 along the line B-B shown in the exploded view 810 of a part of FIG. 8A.

FIG. 8C shows a cross-sectional view of the multi-layer microfluidic chip 800 along the line C-C shown in the exploded view 810 of a part of FIG. 8A The multi-layer microfluidic chip 800 may include separation channels 802a disposed over supporting channels 802b. In the plan view of FIG. 8A, the separation channels 802a and the supporting channels 802b may seem to be on the same level, however, they are disposed on different levels of the multi-layer microfluidic chip 800. As more clearly shown in the cross-sectional views of FIG. 8B and FIG. 8C, the separation channels 802a may be disposed on an upper layer of the multi-layer microfluidic chip 800 and the supporting channels 802b may be disposed on a lower layer of the multi-layer microfluidic chip 800. In other words, the supporting channels 802b may be underneath the separation channels 802a. The separation channels 802a may be filled with a medium for electrophoresis (e.g. gel) and the supporting channels 802b may be filled with a running buffer.

The multi-layer microfluidic chip 800 may include at least one extraction chamber 804. Only one extraction chamber 804 is shown as an example. However the number of extraction chambers may be more than one and may, for example, be two, three, four, or more extraction chambers.

The multi-layer microfluidic chip 800 may include at least one porous structure 812 disposed between the separation channels 802a and the supporting channels 802b (e.g. as shown in FIG. 8B and FIG. 8C).

The separation channels 802a may include a plurality of parallel channels 806a, 806b, e.g. as shown in FIG. 8A. The plurality of parallel channels 806a, 806b of the separation channels 802a may be designed and fabricated on the multi-layer microfluidic chip 800. Only two parallel channels 806a, 806b are shown as an example. However the number of parallel channels may be more than two and may, for example, be three, four, or more parallel channels.

Each parallel channel of the plurality of parallel channels 806a, 806b may be connected to a respective reservoir. For example the parallel channel 806a may be connected to a sample reservoir and the parallel channel 806b may be connected to a reference reservoir. The parallel channel 806a connected to the sample reservoir may be additionally connected to the at least one extraction chamber 804. For example, the parallel channel 806a may be disposed between the sample reservoir and the at least one extraction chamber 804. Accordingly, the parallel channel 806b may be used as a reference channel and the parallel channel 806a connecting to the at least one extraction chamber 804 may be used for separation of target analyte fragments.

Electrodes (not shown in FIG. 8A) may be placed at or on the multi-layer microfluidic chip 800. For example, an electrode may be placed at each of reservoir BR1 and first waste reservoir W1, which may generate an electrical field along the medium (e.g. gel) in the channel (e.g. microfluidic channel) from reservoir BR1 to first waste reservoir W1. The reservoir BR1 and the first waste reservoir W1 may be disposed in the separation channels 802a of the multi-layer microfluidic chip 800. Accordingly, the electrical field may be generated in an upper layer of the multi-layer microfluidic chip 800.

Multiple analyte fragments of the sample may thus separate along the parallel channel 806a towards the first waste reservoir W1, e.g. in the medium (e.g. gel) that may be pre-loaded in the parallel channel 806a. At the same time, a reference analyte fragment may move along the parallel channel 806b towards the first waste reservoir W1. The flow path of the reference analyte fragment between the reference reservoir and the first waste reservoir W1 may intersect with a detection area 808 that may be disposed along the parallel channel 806a. The detection area 808 may be disposed in the parallel channel 806b of the multi-layer microfluidic chip 800.

Once the reference analyte fragment is detected in the detection area 808, the direction of the electrical field is switched from the first direction BR1-W1 to a second direction BR1-W2 towards the at least one extraction chamber 804 and the underneath supporting channel 802b in the bottom layer of the multi-layer microfluidic chip 800, as shown in FIG. 8B and FIG. 8C. For example, an electrode may be placed at a second waste reservoir W2, which may be disposed in the supporting channel 802b of the multi-layer microfluidic chip 800.

FIG. 8B shows a cross-sectional view of the at least one extraction chamber 804 along the line B-B shown in the exploded view 810 of FIG. 8A. FIG. 8C shows a cross-sectional view of the at least one extraction chamber 804 along the line C-C shown in the exploded view 810 of FIG. 8A.

As seen in FIG. 8B and FIG. 8C, at least one porous structure 812 may line one or more sides of the at least one extraction chamber 804. As described above, the interfering materials pass through the at least one porous structure 812 and exit the at least one extraction chamber 804 under the influence of the second voltage applied in the second direction BR1-W2. The at least one target analyte may be stopped from exiting the at least one extraction chamber 804 by means of the at least one porous structure 812. Since the target analyte fragment cannot pass through the at least one porous structure 812, the target analyte fragment is confined within the at least one extraction chamber 804, which may be filled with the same buffer as the running buffer of electrophoresis (e.g. gel electrophoresis).

The at least one porous structure (e.g. extraction membrane) may be embedded in the multi-layer microfluidic chip 800 by means of at least one of hot embossing, thermal bonding, laser bonding, ultrasonic bonding, although other techniques may be possible as well. After embedding, the at least one porous structure (e.g. extraction membrane) may be tightly fit in the multi-layer microfluidic chip 800 to avoid sample loss or cross contamination during the above-described extraction process.

Extraction of multiple analyte fragments can be realized sequentially or simultaneously. As shown in FIG. 8A, once the first reference fragment is detected, the electrical field may be switched from the direction of BR1-W1 to the direction of BR1-W2, and the first target analyte fragment may be collected in the at least one extraction chamber 804.

After the first target analyte fragment is completely moved from the medium (e.g. gel) into the at least one extraction chamber 804, the solution in the at least one extraction chamber 804 containing the first target analyte fragment can be taken out either by a pipette or a pump. Thereafter, a fresh running buffer can be re-filled for the subsequent extractions either by a pipette or a pump. To remove possible residue of the first target analyte fragment that may be left in the at least one extraction chamber 804, rinsing of the at least one extraction chamber 804 can be done by repeating the filling-emptying process with a pipette or pump. Alternatively, it can be realized by applying the electrical field BR2-W1 for a period of time. The minor quantity of first target analyte fragment residue can be completely removed from the extraction buffer toward the first waste reservoir W1 with only the running buffer left. By repeating the separation and extraction steps, multiple target analyte fragments can be collected sequentially.

In another embodiment, extraction can be realized by using flow controllers (e.g. valve elements).

Figures 9A, 9B:
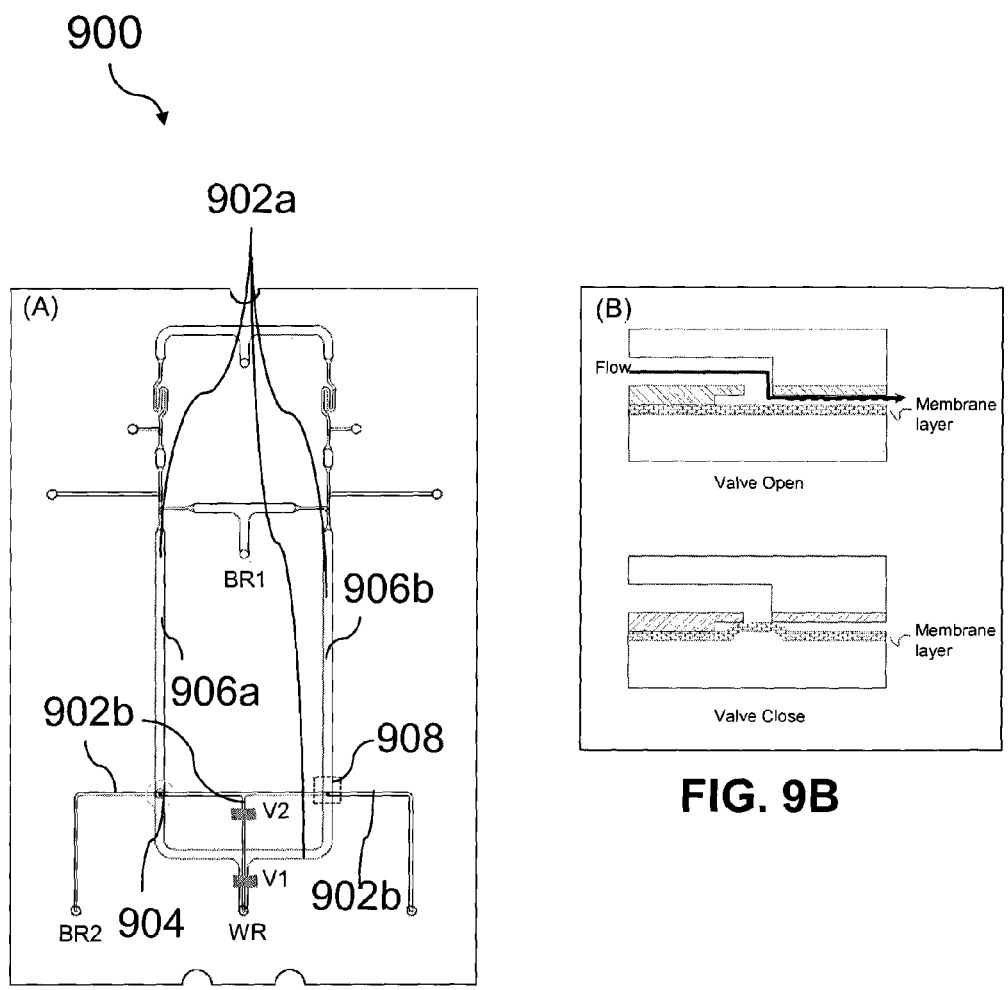
FIG. 9A and FIG. 9B show various views of a multi-layer microfluidic chip including a first flow controller and a second flow controller.

FIG. 9A and FIG. 9B show various views of a multi-layer microfluidic chip 900 including a first flow controller V1 and a second flow controller V2.

Similar to the multi-layer microfluidic chip 800 shown in FIG. 8A to FIG. 8C, the multi-layer microfluidic chip 900 may include separation channels 902a disposed over supporting channels 902b. In the plan view of FIG. 9A, the separation channels 902a and the supporting channels 902b may seem to be on the same level, however, they are disposed on different levels of the multi-layer microfluidic chip 900. In other words, similar to the microfluidic chip 800, the supporting channels 902b may be underneath the separation channels 902a. The separation channels 902a may be filled with a medium for electrophoresis (e.g. gel) and the supporting channels 902b may be filled with a running buffer.

The first flow controller V1 may be disposed in the separation channels 902a (i.e. the upper layer) of the multi-layer microfluidic chip 900. The second flow controller V2 may be disposed in the supporting channels 902b (i.e. the lower layer) of the multi-layer microfluidic chip 900.

Similar to the multi-layer microfluidic chip 800 shown in FIG. 8A to FIG. 8C, the separation channels 902a may include a plurality of parallel channels 906a, 906b, e.g. as shown in FIG. 9A. The plurality of parallel channels 906a, 906b may be designed and fabricated on the multi-layer microfluidic chip 900. Only two parallel channels 906a, 906b are shown as an example. However the number of parallel channels may be more than two and may, for example, be three, four, or more parallel channels.

Each parallel channel of the plurality of parallel channels 906a, 906b may be connected to a respective reservoir. For example the parallel channel 906a may be connected to a sample reservoir and the parallel channel 906b may be connected to a reference reservoir. The parallel channel 906a connected to the sample reservoir may be additionally connected to the at least one extraction chamber 904. For example, the parallel channel 906a may be disposed between the sample reservoir and the at least one extraction chamber 904. Accordingly, the parallel channel 906b may be used as a reference channel and the parallel channel 906a connecting to the at least one extraction chamber 904 may be used for separation of target analyte fragments.

Electrodes (not shown in FIG. 9A) may be placed at or on the multi-layer microfluidic chip 900. For example, an electrode may be placed at each of reservoir BR1 and the waste reservoir WR, which may generate an electrical field along the medium (e.g. gel) in the channel (e.g. microfluidic channel) from reservoir BR1 to the waste reservoir WR. The reservoir BR1 may be disposed in the separation channels 902a of the multi-layer microfluidic chip 900, while the waste reservoir WR may be disposed in the supporting channels 902b of the multi-layer microfluidic chip 900. Accordingly, the electrical field may be generated from an upper layer of the multi-layer microfluidic chip 900 to a lower layer of the multi-layer microfluidic chip 900. For example, the plurality of parallel channels 906a, 906b and the underneath supporting channels 902b may be connected to the same waste reservoir WR.

When the first flow controller V1 disposed in the separation channels 902a is opened, while second flow controller V2 in the supporting channels 902b is closed, and when voltage is applied, an electrical field is created along the microfluidic channel from reservoir BR1 to waste reservoir WR. At least one target analyte fragment and at least one reference analyte fragment are thus separated in the medium (e.g. gel matrix) pre-loaded in the parallel channels 906a and 906b respectively of the top layer of the multi-layer microfluidic chip 900 towards the waste reservoir WR.

Once the first reference analyte fragment is detected in the detection area 908, the first flow controller V1 (e.g. valve element) may subsequently be closed and second flow controller V2 (e.g. valve element) may subsequently be opened. The electrical field is still created along the microfluidic channel from reservoir BR1 to waste reservoir WR. However, in this case, the electrical field is created along the underneath supporting channels 902b from reservoir BR1 toward waste reservoir WR. The target analyte fragment may then be extracted in the extraction chamber 904. After the extraction is completed, a pipette or a pump is used for the first target analyte fragment collection and fresh buffer re-filling.

After this the second flow controller V2 (e.g. valve element) may be closed and the first flow controller V1 (e.g. valve element) may be opened and the electrical field direction will be switched back along the upper separation channels 902a. When the second reference analyte fragment is detected in the detection area 908, the first flow controller V1 (e.g. valve element) may be closed again and the second flow controller V2 (e.g. valve element) may be opened for the extraction of the second target analyte fragment. This process may be repeated for a third reference analyte fragment and a third target analyte fragment, and so forth.

To remove possible analyte residue left in the extraction chamber 904, rinsing of the extraction chamber 904 can be done by repeating the filling-emptying process with a pipette or pumps. Alternatively, it can also be realized by applying the electrical field from a buffer reservoir BR2 towards the waste reservoir WR for a period of time.

Figure 10:
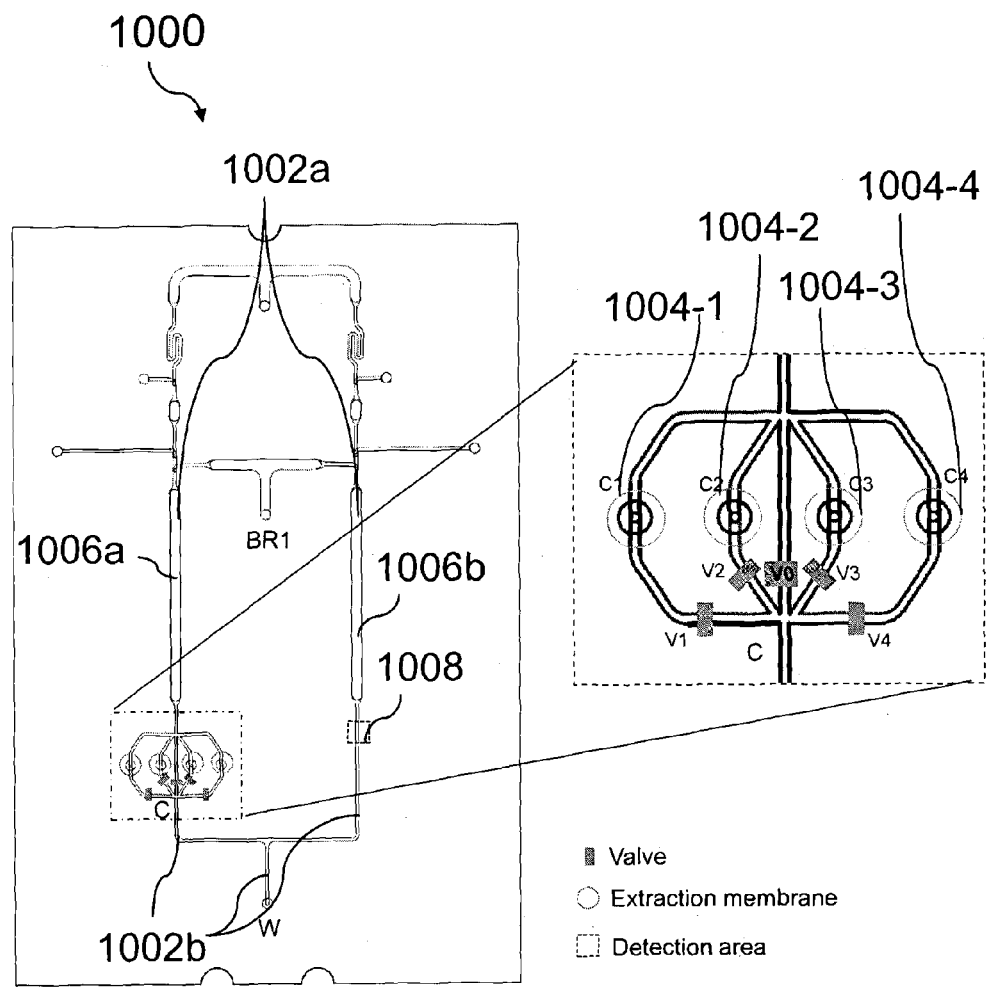
FIG. 10 shows a plan view of a multi-layer microfluidic chip including a plurality of flow controllers and a plurality of extraction chambers.

In another embodiment, multiple target analyte fragments may be extracted simultaneously by using a plurality of flow controllers (e.g. valve elements) V0 to V4, as shown in FIG. 10.

FIG. 10 shows a plan view of a multi-layer microfluidic chip 1000 including a plurality of flow controllers V0 to V4 and a plurality of extraction chambers C1 to C4.

Similar to the multi-layer microfluidic chip 800 shown in FIG. 8A to FIG. 8C, the multi-layer microfluidic chip 1000 may include separation channels 1002a disposed over supporting channels 1002b. In the plan view of FIG. 10, the separation channels 1002a and the supporting channels 1002b may seem to be on the same level, however, they are disposed on different levels of the multi-layer microfluidic chip 1000. For example, in an analogous manner to that shown in the cross-sectional view of FIG. 8B and FIG. 8C, the separation channels 1002a may be disposed on an upper layer of the multi-layer microfluidic chip 1000 and the supporting channels 1002b may be disposed on a lower layer of the multi-layer microfluidic chip 1000. In other words, the supporting channels 1002b may be underneath the separation channels 1002a. The separation channels 1002a may be filled with a medium for electrophoresis (e.g. gel) and the supporting channels 1002b may be filled with a running buffer.

Similar to the multi-layer microfluidic chip 800 shown in FIG. 8A to FIG. 8C, the separation channels 1002a may include a plurality of parallel channels 1006a, 1006b, e.g. as shown in FIG. 10. The plurality of parallel channels 1006a, 1006b may be designed and fabricated on the multi-layer microfluidic chip 1000. Only two parallel channels 1006a, 1006b are shown as an example. However the number of parallel channels may be more than two and may, for example, be three, four, or more parallel channels.

Each parallel channel of the plurality of parallel channels 1006a, 1006b may be connected to a respective reservoir. For example the parallel channel 1006a may be connected to a sample reservoir and the parallel channel 1006b may be connected to a reference reservoir. The parallel channel 1006a connected to the sample reservoir may be additionally connected to the plurality of extraction chambers C1 to C4. For example, the parallel channel 1006a may be disposed between the sample reservoir and the plurality of extraction chambers C1 to C4. Accordingly, the parallel channel 1006b may be used as a reference channel and the parallel channel 1006a connecting to the plurality of extraction chambers C1 to C4 may be used for separation of target analyte fragments.

The flow controller V0 may be disposed in the separation channels 1002a of the multi layer microfluidic chip 1000. The plurality of flow controllers V1 to V4 may be disposed in the supporting channels 1002b of the multi-layer microfluidic chip 1000. The plurality of extraction chambers C1 to C4 may be disposed in the supporting channels 1002b of the multi-layer microfluidic chip 1000.

A respective porous structure 1004-1 to 1004-4 may line at least one side of a respective extraction chamber of the plurality of extraction chambers C1 to C4. The respective porous structures 1004-1 to 1004-4 may, for example, be disposed between the separation channels 1002a and the supporting channels 1002b of the multi-layer microfluidic chip 1000. The respective porous structures 1004-1 to 1004-4 may, for example, be additionally disposed in the separation channels 1002a of the multi-layer microfluidic chip 1000 over an area spanning the underlying extraction chambers C1 to C4.

An electrode may be placed in the buffer at each of reservoir BR1 and waste reservoir W to provide an electrical field in the direction of BR1-W through the buffer in the gel along the microfluidics channel.

At first, all flow controllers (e.g. valve elements) V0 to V4 may be closed except the flow controller V0 which may be connected with the channel branch without an extraction chamber, as shown in FIG. 10.

When the first reference analyte fragment is detected in the detection area 1008, the flow controller V1 (e.g. valve element) on the supporting channel branch connecting to the extraction chamber C1 may be opened while all the other flow controllers (e.g. valves) may be closed. The first target analyte fragment may then be transferred into the separation channel branch leading to the extraction chamber C1, e.g. disposed in the supporting channels 1002b of the multi-layer microfluidic chip 1000.

Thereafter, the flow controller V0 (e.g. valve element) may be opened and all other flow controllers (e.g. valve elements) may be closed. When the second reference analyte fragment is detected in the detection area 1008, the flow controller V2 (e.g. valve element) on the supporting channel branch connecting to the extraction chamber C2 is opened, while all the other flow controllers (e.g. valves) may be closed. The second target analyte fragment may then be transferred into the separation channel branch leading to the extraction chamber C2, e.g. disposed in the supporting channels 1002b of the multi-layer microfluidic chip 1000. This process may be repeated for the third reference analyte fragment, the third target analyte fragment, and all subsequent reference and/or target analyte fragments.

After all target analyte fragments are transferred into respective separation channels, all flow controllers V0 to V4 may be opened to extract all target analyte fragments into the respective extraction chambers C1 to C4, e.g. disposed in the supporting channels 1002b of the multi-layer microfluidic chip 1000.

Alternatively, a selective microvalve can be implemented at point C shown in FIG. 10. In such an example, the selective microvalve may open a path without an extraction chamber for the separation of target analyte fragments. When the first reference analyte fragment is detected in the detection area 1008, the selective microvalve at point C may open a path from extraction chamber C1 to the waste reservoir W to transfer the first target analyte fragment into the separation channel branch leading to the extraction chamber C1. When the second reference analyte fragment is detected, the selective microvalve at point C may open a path from extraction chamber C2 to waste reservoir W to transfer the second target analyte fragment into the separation channel branch leading to the extraction chamber. C2. This process may be repeated for subsequent reference analyte fragments and subsequent target analyte fragments.

An experiment was performed on the above-described multi-layer microfluidic chips 800, 900, 1000 to sequentially extract three DNA fragments of molecular-weights 200 bp, 500 bp and 1 kb.

Figures 11A, 11B, 11C, 11D:
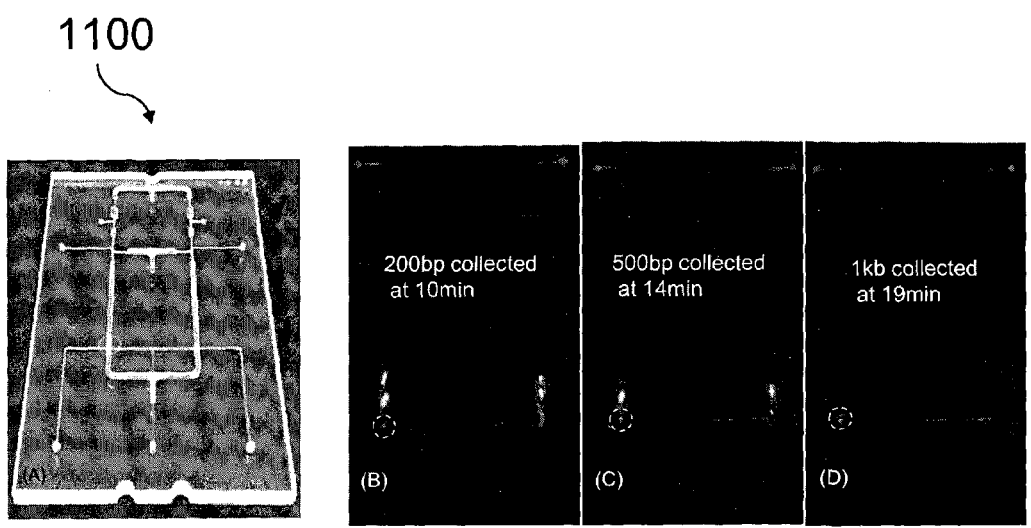
FIG. 11A shows a photograph of a multi-DNA extraction chip used in an analyte extraction experiment and FIG. 11B to FIG. 11D show results of the experiment.

FIG. 11A shows a photograph of a multi-DNA extraction chip 1100 used in the experiment and FIG. 11B to FIG. 11D show results of the experiment.

As shown in FIG. 11B to FIG. 11D, the three DNA fragments of 200 bp, 500 bp and 1 kb were completely extracted from the medium (e.g. gel matrix) in the separation channel at 10 min, 14 min and 19 min, respectively. This is much faster compared to the conventional DNA extraction from a medium (e.g. gel matrix), which usually takes more than 3 hours from medium casting (e.g. gel casting) to DNA purification and extraction from the medium (e.g. gel). Moreover, the operation can be significantly simplified without using extra reagents or devices for DNA extraction from the medium (e.g. gel matrix). For example, an operator only needs to load the sample and reference, run the system and collect the extracted target analyte fragment (e.g. DNA fragment), e.g. with a pipette, sequentially when each individual extraction is finished.

Figure 12:
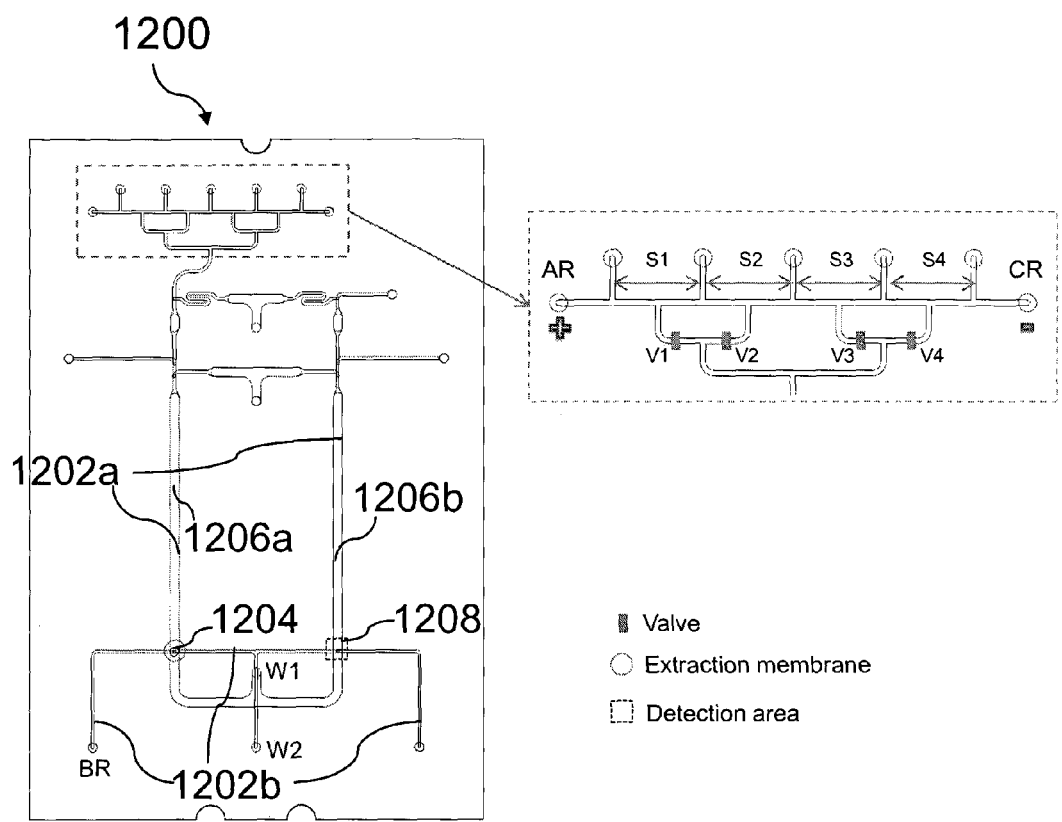
FIG. 12 shows a plan view of a two-dimensional separation-extraction microfluidic chip.

FIG. 12 shows a plan view of a two-dimensional separation-extraction microfluidic chip 1200.

Similar to the multi-layer microfluidic chip 800 shown in FIG. 8A to FIG. 8C, the multi-layer microfluidic chip 1200 may include separation channels 1202a disposed over supporting channels 1202b. In the plan view of FIG. 12, the separation channels 1202a and the supporting channels 1202b may seem to be on the same level, however, they are disposed on different levels of the multi-layer microfluidic chip 1200. For example, in an analogous manner to that shown in the cross-sectional views of FIG. 8B, and FIG. 8C, the separation channels 1202a may be disposed on an upper layer of the multi-layer microfluidic chip 1200 and the supporting channels 1202b may be disposed on a lower layer of the multi-layer microfluidic chip 1200. In other words, the supporting channels 1202b may be underneath the separation channels 1202a. The separation channels 1202a may be filled with a medium for electrophoresis (e.g. gel) and the supporting channels 1202b may be filled with a running buffer.

In the embodiment shown in FIG. 12, extraction of target analyte fragments like protein biomarkers from complicated samples may be done in two dimensions. The first dimension may be in the direction between an anodic reservoir AR and a cathodic reservoir CR. For example, a sample protein mixture may be focused at their respective isoelectric point in the first dimension between the anodic reservoir AR and cathodic reservoir CR by means of isoelectric focusing (IEF). The second dimension may be the above-described electrophoresis (e.g. gel electrophoresis) toward the first waste reservoir W1 to further separate the proteins of the sample according to their sizes.

The anodic reservoir AR and the cathodic reservoir CR may be connected by means of an IEF channel. The IEF channel may be divided into a plurality of segments S1, S2, ..., Sn. In the example shown in FIG. 12, the IEF channel may be divided into four segments S1, S2, S3, S4. Proteins with at least substantially similar isoelectric points may be focused at the same segments along the IEF channel between the anodic reservoir AR and the cathodic reservoir CR.

A target protein fragment may be extracted from proteins having at least substantially similar isoelectric points by means of its molecular weight (e.g. size), and this may be performed in the second dimension by means of electrophoresis (e.g. gel electrophoresis).

Contents of the segment S1, S2, S3, S4 of the IEF channel between the anodic reservoir AR and the cathodic reservoir CR containing the target analyte fragment may be transferred into the second dimension by opening the respective individual flow controller (e.g. control valve). For example, the contents of segment S1 may be transferred into the second dimension by means of flow controller V1; the contents of segment S2 may be transferred into the second dimension by means of flow controller V2; the contents of segment S3 may be transferred into the second dimension by means of flow controller V3; the contents of segment S4 may be transferred into the second dimension by means of flow controller V4.

Similar to the multi-layer microfluidic chips 800, 900, 1000 described above, the separation channels 1202a may include a plurality of parallel channels 1206a, 1206b, e.g. as shown in FIG. 12. The plurality of parallel channels 1206a, 1206b may be designed and fabricated on the chip 1200. Only two parallel channels 1206a, 1206b are shown as an example. However the number of parallel channels may be more than two and may, for example, be three, four, or more parallel channels.

Each parallel channel of the plurality of parallel channels 1206a, 1206b may be connected to a respective reservoir. For example the parallel channel 1206a may be connected to a sample reservoir that may include the IEF channel, the anodic reservoir AR, and the cathodic reservoir CR. The parallel channel 1206b may be connected to a reference reservoir.

As shown in FIG. 12, the parallel channel 1206a connected to the sample reservoir may be additionally connected to the at least one extraction chamber 1204. For example, the parallel channel 1206a may be disposed between the sample reservoir (that may include the IEF channel, the anodic reservoir AR, and the cathodic reservoir CR) and the at least one extraction chamber 1204. Accordingly, the parallel channel 1206b may be used as a reference channel and the parallel channel 1206*a* connecting to the at least one extraction chamber 1204 may be used for separation of target analyte fragments.

In the second dimension, the separation of the contents of the transferred segment may be done simultaneously with the reference in the parallel channel 1206*b*. When a reference analyte fragment is detected in the detection area 1208, extraction of the target analyte fragment may be triggered to obtain pure protein fragment in the extraction chamber 1204.

If there are more than one target protein fragment in the sample, multiple extraction can also be realized subsequently or simultaneously by repeating the above described extraction procedures in a single extraction chamber 1204 (e.g. in respect of FIG. 8 and FIG. 9) or multiple extraction chambers (e.g. in respect of FIG. 10).

According to various embodiments presented herein, a detection system may be used to actively locate a desired analyte fragment and switch the direction of an applied voltage to drive the desired analyte fragments to at least one extraction chamber.

According to various embodiments presented herein, a detection system may be used to actively locate a desired analyte fragment and a flow controller (e.g. valve element) may be used to control the flow and the direction of an electrical field to drive the desired analyte fragments to at least one extraction chamber.

According to various embodiments presented herein, an active extraction mechanism can be used to extract multiple analyte fragments.

According to various embodiments presented herein, a desired analyte fragment may be collected in an extraction chamber lined with a porous structure (e.g. extraction membrane) with acceptable purity.

According to various embodiments presented herein, multiple analyte extraction can be quickly realized on a microfluidic chip with parallel separation channels, at least one extraction chamber disposed above an embedded porous structure (e.g. embedded extraction membrane).

According to various embodiments presented herein, a system extracting one or more analyte fragments from a gel matrix may be provided. The system may include a power supply for running electrophoresis; an active detection system for collecting a reference signal (e.g. generated in response to detection of a reference analyte fragment); a software to trigger the start of extraction by switching the direction of an electrical field and a cartridge which includes an extraction chamber and an extraction membrane lining at least one side of the extraction chamber. The reference signal may trigger the extraction after the target analyte fragment is separated from interfering materials during electrophoresis. The analyte fragment may be driven towards the extraction chamber, being stopped by the extraction membrane, and extracted from the gel. The cartridge may include a chamber frame to produce chambers in gel, a membrane frame and an extraction membrane sandwiched between the two frames.

According to various embodiments presented herein, a system for extracting one or more analyte fragments from a gel matrix may be provided. The system may include a power supply for running electrophoresis; a detection system for detecting a reference signal (e.g. generated in response to detection of a reference analyte fragment); and a microfluidic device including an extraction chamber and an extraction membrane. The reference signal may trigger the extraction after the target analyte fragment is separated from interfering materials during electrophoresis. The extraction membrane in the microfluidic device can be embedded by thermal bonding, hot embossing, laser bonding, ultrasonic bonding or other methods to tightly attach the membrane to the microfluidic device.

According to various embodiments presented herein, a microfluidic device may be provided. The microfluidic device may include a reference channel with gel for reference; a separation channel with gel for separation of analyte sample; an extraction chamber with extraction membrane connected to supporting channel; and a first waste reservoir connecting to the separation channel and a waste reservoir connecting to the supporting channel. The target analyte fragment may move to the extraction chamber, being stopped by the extraction membrane, and extracted from the gel after the electrical field is applied from the separation channel to the extraction chamber. The electrical field may be applied by switching the positive electrode from the first waste reservoir to the second waste reservoir.

According to various embodiments presented herein, a microfluidic device may be provided. The microfluidic device may include a reference channel with gel for reference; a separation channel with gel for separation of analyte sample; an extraction chamber with extraction membrane connected to supporting channel; a first valve on the separation channel and a second valve on the supporting channel; and a waste reservoir connecting to the separation channel when the first valve opens and the second valve closes; the waste reservoir connecting to the supporting channel when the first valve closes and the second valve opens. The target analyte fragment moves to the extraction chamber, being stopped by the extraction membrane, and extracted from the gel after the electrical field is applied from the separation channel to the extraction chamber. The electrical field is applied by closing the first valve and opening the second valve. The extraction chamber can be re-used for multiple analyte fragments extraction, with the rinsing procedure to remove the minor quantity of analyte residue. The rinsing procedure can be realized by repeating filling and emptying running buffer in the extraction chamber for several times with pipette or pumps. The rinsing procedure can also be realized by switching the electrical field to rinse the extraction chamber with clean running buffer for some time.

According to various embodiments presented herein, a system for extracting multiple analyte fragments from a gel matrix may be provided. The system may include a power supply for running electrophoresis; a detection system for detecting reference signal; and a microfluidic device including multiple extraction chambers and extraction membranes. The reference signal triggers the extraction after the target analyte fragment is separated from interfering materials during electrophoresis. The extraction membrane in the microfluidic device can be embedded by thermal bonding, hot embossing, laser bonding, ultrasonic bonding or other methods to tightly attach the membrane to the microfluidic device.

According to various embodiments presented herein, a microfluidic device may be provided. The microfluidic device may include a reference channel with gel for loading reference fragments; a separation channel with gel for loading analyte sample; multiple separation channel branches at the end of the separation channel; each the separation channel branch leading to an extraction chamber and one the branch leading to a waste reservoir with a valve to control the fluid flow in the branch; each of the extraction chambers with extraction membrane connecting to a supporting channel branch; the supporting channel branches connecting to the waste reservoir. One valve on each the supporting channel branch to open or close the fluid flow in the channel branch. The waste reservoir connecting to the separation channel branch when the valve opens and the rest of the valves close. The target analyte fragment moves to a the extraction chamber, being stopped by the extraction membrane, and extracted from the gel after the electrical field is applied from the separation channel to the extraction chamber. The electrical field is applied by closing all the valves except the one on the supporting channel branch connecting to the extraction chamber. The multiple analyte fragments extraction can be realized by replacing the multiple valves with a selective valve before the waste reservoir. The analyte fragment separation can be accomplished in one dimension or in multi-dimensions according to different separation mechanism. The detection system may be a optical system. The gel can be agrose, polyacrylamide or any solidified gel matrix. The analyte fragments can be DNAs, RNAs, proteins or any large molecules which can be separated by gel electrophoresis and extracted by the appropriate the extraction membrane from the gel.

According to various examples presented herein, a device for extracting at least one analyte is provided. The device includes a sample reservoir configured to contain a sample comprising at least one target analyte and interfering materials; at least one extraction chamber connected to the sample reservoir; at least one porous structure lining one or more sides of the at least one extraction chamber; and a voltage source configured to provide a first voltage and a second voltage, wherein, when the first voltage is provided, the at least one target analyte and the interfering materials move into the at least one extraction chamber or to a predetermined area from the at least one extraction chamber, wherein, when the second voltage is provided, the interfering materials pass through and exit the at least one extraction chamber, and the at least one target analyte is stopped from exiting the at least one extraction chamber by means of the at least one porous structure.

The first voltage is provided in a first direction and the second voltage is provided in a second direction different from the first direction.

The voltage source is configured to switch from the first voltage to the second voltage upon detection of a reference analyte by a detector.

The device further comprises the detector.

The detector is configured to provide a trigger for switching from the first voltage to the second voltage to the voltage source upon detection of the reference analyte.

The device may be configured as a microfluidic chip.

The device may further include a first waste reservoir; a second waste reservoir; wherein the first voltage is applied between the sample reservoir and the first waste reservoir, and wherein is applied between the sample reservoir and the second waste reservoir.

The device may further include a separation channel disposed at a first level; and a supporting channel disposed at a second level disposed below the first level, wherein the first waste reservoir is disposed at the first level and the second waste reservoir is disposed at the second level.

The at least one extraction chamber is disposed at the first level, and wherein the at least one porous structure is disposed between the first level and the second level and lines at least one side of the at least one extraction chamber.

According to various examples presented herein, a device for extracting at least one analyte is provided. The device may include a sample reservoir configured to contain a sample comprising at least one target analyte and interfering materials; at least one extraction chamber connected to the sample reservoir; at least one porous structure lining one or more sides of the at least one extraction chamber; a first flow controller disposed along a first channel extending from the at least one extraction chamber; and a second flow controller disposed along a second channel extending from the at least one extraction chamber, wherein, when the first flow controller is open and the second flow controller is closed, the at least one target analyte and the interfering materials move into the at least one extraction chamber under the influence of a voltage, and wherein, when the first flow controller is closed and the second flow controller is open, the interfering materials pass through the at least one porous structure and exit the at least one extraction chamber under the influence of the voltage, the at least one target analyte being stopped from exiting the at least one extraction chamber by means of the at least one porous structure.

The first channel is disposed at a first level and the second channel is disposed at a second level below the first level.

The device may further include a voltage source configured to provide the voltage.

The device may further include a waste reservoir connected to each of the first channel and the second channel, wherein the voltage is applied from the sample reservoir to the waste reservoir.

The device is further configured to close the first flow controller and open the second flow controller upon detection of a reference analyte by a detector.

The device may further include the detector.

The detector is configured to close the first flow controller and open the second flow controller upon detection of the reference analyte.

The device may be configured as a microfluidic chip.

Each of the first flow controller and the second flow controller comprises a valve.

According to various examples presented herein, a device for extracting a plurality of analytes is provided. The device may include: a sample reservoir configured to contain a sample comprising at least one target analyte and interfering materials; a plurality of extraction chambers connected to the sample reservoir, wherein each extraction chamber is connected to the sample reservoir by means of a respective separation channel branch; a respective porous structure lining one or more sides of a respective extraction chamber; a respective flow controller disposed along a respective separation channel branch and configured to control flow along the respective separation channel branch; and a voltage source configured to provide a voltage.

The device may further include a waste reservoir connected to each extraction chamber of the plurality of extraction chambers, wherein the voltage is applied from the sample reservoir to the waste reservoir.

While various aspects have been particularly shown and described with reference to these aspects of this disclosure, it should be understood by those skilled in the art that various changes in form and detail may be made therein without departing from the spirit and scope of the disclosure as defined by the appended claims. The scope of the disclosure is thus indicated by the appended claims and all changes which come within the meaning and range of equivalency of the claims are therefore intended to be embraced.

What is claimed is:
1. A device for extracting at least one analyte, the device comprising:
 a sample reservoir configured to contain a sample comprising at least one target analyte and interfering materials;

a reference reservoir configured to contain a reference comprising at least one reference analyte, wherein the at least one reference analyte is sized substantially similar to the at least one target analyte;

at least one extraction chamber connected to the sample reservoir;

at least one porous structure lining one or more sides of the at least one extraction chamber; and a voltage source configured to provide a first voltage and a second voltage, wherein, when the first voltage is provided, the at least one target analyte, the interfering materials and the at least one reference analyte move towards the at least one extraction chamber or to a predetermined area near the at least one extraction chamber, wherein, when the second voltage is provided, the interfering materials pass through and exit the at least one extraction chamber, and the at least one target analyte is stopped from exiting the at least one extraction chamber by means of the at least one porous structure;

and wherein the voltage source is configured to switch from the first voltage to the second voltage upon detection of the at least one reference analyte by a detector.

2. The device of claim 1, wherein the first voltage is provided in a first direction and the second voltage is provided in a second direction different from the first direction.

3. The device of claim 1, further comprising the detector.

4. The device of claim 3, wherein the detector is configured to provide a trigger for switching from the first voltage to the second voltage to the voltage source upon detection of the reference analyte.

5. The device of claim 1, configured as a microfluidic chip.

6. The device of claim 1, further comprising:
a first waste reservoir;
a second waste reservoir;
wherein the first voltage is applied between the sample reservoir and the first waste reservoir, and wherein the second voltage is applied between the sample reservoir and the second waste reservoir.

7. The device of claim 6, further comprising:
a separation channel disposed at a first level; and
a supporting channel disposed at a second level disposed below the first level,
wherein the first waste reservoir is disposed at the first level and the second waste reservoir is disposed at the second level.

8. The device of claim 7, wherein the at least one extraction chamber is disposed at the first level, and wherein the at least one porous structure is disposed between the first level and the second level and lines at least one side of the at least one extraction chamber.

9. A device for extracting at least one analyte, the device comprising:
a sample reservoir configured to contain a sample comprising at least one target analyte and interfering materials;
a reference reservoir configured to contain a reference comprising at least one reference analyte, wherein the at least one reference analyte is sized substantially similar to the at least one target analyte; at least one extraction chamber connected to the sample reservoir;
at least one porous structure lining one or more sides of the at least one extraction chamber;
a first flow controller disposed along a first channel extending from the at least one extraction chamber; and
a second flow controller disposed along a second channel extending from the at least one extraction chamber,
wherein, when the first flow controller is open and the second flow controller is closed, the at least one target analyte, the interfering materials and the at least one reference analyte move towards the at least one extraction chamber under the influence of a voltage, and
wherein, when the first flow controller is closed and the second flow controller is open, the interfering materials pass through the at least one porous structure and exit the at least one extraction chamber under the influence of the voltage, the at least one target analyte being stopped from exiting the at least one extraction chamber by means of the at least one porous structure,
wherein, the first flow controller is configured to close and the second flow controller is configured to open when at least one reference analyte is detected by a detector.

10. The device of claim 9, wherein the first channel is disposed at a first level and the second channel is disposed at a second level below the first level.

11. The device of claim 9, further comprising:
a voltage source configured to provide the voltage.

12. The device of claim 11 further comprising:
a waste reservoir connected to each of the first channel and the second channel,
wherein the voltage is applied from the sample reservoir to the waste reservoir.

13. The device of claim 9, further comprising the detector.

14. The device of claim 13, wherein the detector is configured to close the first flow controller and open the second flow controller upon detection of the reference analyte.

15. The device of claim 9, configured as a microfluidic chip.

16. The device of claim 9, wherein each of the first flow controller and the second flow controller comprises a valve.

17. A device for extracting a plurality of analytes, the device comprising:
a sample reservoir configured to contain a sample comprising at least one target analytes and interfering materials;
a reference reservoir configured to contain a reference comprising a plurality of reference analytes, wherein each reference analyte of the plurality of reference analytes is sized substantially similar to a respective target analyte of the plurality of target analytes;
a plurality of extraction chambers connected to the sample reservoir, wherein each extraction chamber is connected to the sample reservoir by means of a respective separation channel branch;
a respective porous structure lining one or more sides of a respective extraction chamber,
a respective flow controller disposed along a respective separation channel branch and configured to control flow along the respective separation channel branch; and
a voltage source configured to provide a voltage,
wherein, the respective flow controller is configured to open when a respective reference analyte of the plurality of reference analytes is detected by a detector.

18. The device of claim 17, further comprising a waste reservoir connected to each extraction chamber of the plurality of extraction chambers, wherein the voltage is applied from the sample reservoir to the waste reservoir.

* * * * *